(12) United States Patent
Filser et al.

(10) Patent No.: US 8,471,033 B2
(45) Date of Patent: Jun. 25, 2013

(54) METHOD FOR PRODUCING AN INTERMEDIATE PRODUCT OF DABIGATRAN ETEXILATE

(75) Inventors: Christian Filser, Bodenheim (DE); Wolfgang Dersch, Ingelheim (DE); Rainer Hamm, Ingelheim (DE); Arndt Hausherr, Mainz (DE); Gunter Koch, Schwabenheim (DE); Ulrich Scholz, Bad Kreuznach (DE); Georg Zerban, Ingelheim (DE)

(73) Assignee: Boehringer Ingelheim International GmbH, Ingelheim am Rhein ( * ) Notice: Subject to any disclaimer, the term of this patent is extended or adjusted under 35 U.S.C. 154(b) by 211 days.

(21) Appl. No.: 12/997,101

(22) PCT Filed: Jun. 12, 2009

(86) PCT No.: PCT/EP2009/057266
§ 371 (c)(1),
(2), (4) Date: Jan. 27, 2011

(87) PCT Pub. No.: WO2009/153215
PCT Pub. Date: Dec. 23, 2009

(65) Prior Publication Data
US 2011/0118471 A1   May 19, 2011

(30) Foreign Application Priority Data
Jun. 16, 2008   (EP) .................................... 08158364

(51) Int. Cl.
*C07D 401/12* (2006.01)

(52) U.S. Cl.
USPC ..................................................... 546/273.4

(58) Field of Classification Search
USPC ..................................................... 546/273.4
See application file for complete search history.

(56) References Cited

U.S. PATENT DOCUMENTS

| | | | |
|---|---|---|---|
| 7,459,566 B2 | 12/2008 | Zerban et al. | |
| 7,880,016 B2 | 2/2011 | Zerban et al. | |
| 8,119,810 B2 | 2/2012 | Broeder et al. | |
| 2007/0149589 A1 | 6/2007 | Zerban et al. | |
| 2007/0185173 A1 | 8/2007 | Zerban et al. | |
| 2007/0185333 A1 | 8/2007 | Zerban et al. | |
| 2010/0099882 A1 | 4/2010 | Broeder et al. | |
| 2010/0210845 A1 | 8/2010 | Zerban et al. | |
| 2011/0123635 A1 | 5/2011 | Radtke | |
| 2011/0129538 A1 | 6/2011 | Landerer et al. | |
| 2011/0275824 A1 | 11/2011 | Gnad et al. | |
| 2011/0295018 A1 | 12/2011 | Heddesheimer et al. | |
| 2012/0116089 A1 | 5/2012 | Broeder et al. | |
| 2012/0276206 A1 | 11/2012 | Maier | |

FOREIGN PATENT DOCUMENTS

| | | |
|---|---|---|
| WO | 2006/000353 A1 | 1/2006 |
| WO | 2007/071742 A1 | 6/2007 |
| WO | 2007071743 A1 | 6/2007 |
| WO | 2008095928 A1 | 8/2008 |
| WO | 2009118321 A1 | 10/2009 |
| WO | 2009118322 A1 | 10/2009 |
| WO | 2009153214 A1 | 12/2009 |
| WO | 2010007016 A1 | 1/2010 |
| WO | 2011061080 A1 | 5/2011 |

OTHER PUBLICATIONS

International Search Report for PCT/EP2009/057266 mailed Apr. 8, 2009.

*Primary Examiner* — Patricia L Morris
(74) *Attorney, Agent, or Firm* — Michael P. Morris; Wendy A. Petka

(57) ABSTRACT

The invention relates to a process for preparing the compound of formula 1

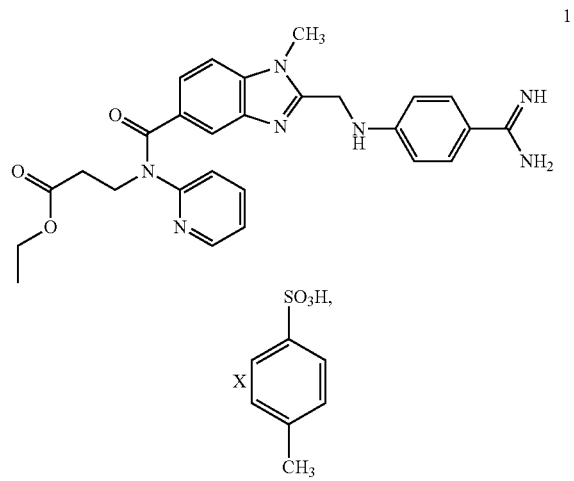

a valuable intermediate product in the synthesis of the pharmaceutical active substance dabigatran etexilate.

5 Claims, No Drawings

METHOD FOR PRODUCING AN INTERMEDIATE PRODUCT OF DABIGATRAN ETEXILATE

This application is the national phase entry under 35 U.S.C. §371 of International Application No. PCT/EP2009/057266, filed Jun. 12, 2009, which claims priority to European Patent Application No. 08158364.3, filed Jun. 16, 2008, the contents of which are hereby incorporated by reference in their entireties.

The invention relates to a process for preparing the compound of formula 1

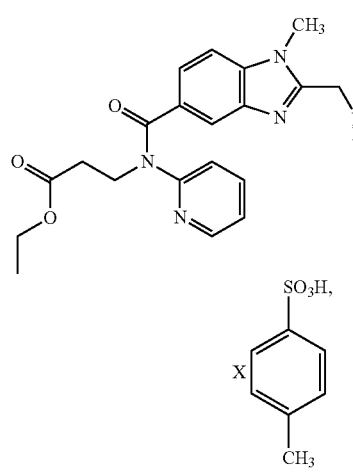

a valuable intermediate product in the synthesis of the pharmaceutical active substance dabigatran etexilate.

PRIOR ART

Dabigatran etexilate is known in the prior art and was first disclosed in International Patent Application WO 98/37075. Processes for preparing dabigatran etexilate are also known from WO 2006/000353 or from Hauel et al. (J. Med. Chem., 2002, 45, 1757 ff).

As can be seen from WO 98/37075 or WO 2006/000353, the compound of formula 1, the 1-methyl-2-[N-[4-amidinophenyl]-amino-methyl]-benzimidazol-5-yl-carboxylic acid-N-(2-pyridyl)-N-(2-ethoxycarbonylethyl)-amide-p-toluenesulphonic acid salt, is of central importance in the synthesis of dabigatran etexilate as an intermediate product.

In addition to International Patent Applications WO 98/37075 and WO 2006/000353, WO 2007/071742 A1 and WO 2007/071743 A1 also disclose aspects of possible methods of preparing dabigatran etexilate.

It is proposed in WO 98/37075 to prepare the substituted (4-benzimidazol-2-ylmethylamino)-benzamidine by reacting the corresponding substituted (4-benzimidazol-2-ylmethylamino)-benzonitrile with ammonia. This process is very demanding in terms of production technology and results in a high load of acids requiring disposal.

In Patent Applications WO 2006/000353 A1, WO 2007/071742 A1 and WO 2007/071743 A1 the compound of formula 1 is prepared through the synthesis of the condensation product of formula 4, as shown in the following Scheme 1.

Scheme 1:

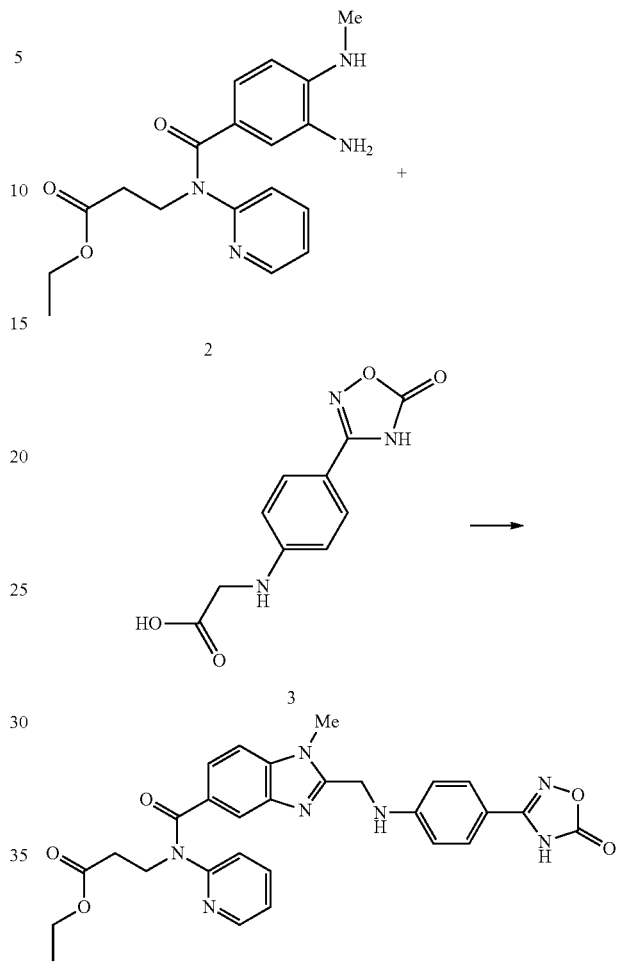

The compound of formula 4 is first of all isolated and then hydrogenated, according to the methods described in the prior art.

In the condensation according to Scheme 1 the by-product of formula 5 is often obtained, and this has to be removed in a laborious hot filtration process before the isolation of the condensation product 4.

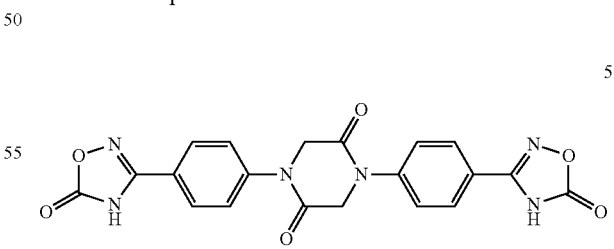

In addition, the further reaction to form the compound of formula 1 requires a change of solvent and additionally very time-consuming and expensive isolation and drying of the intermediate 4. This may be associated with high losses of yield.

The aim of the present invention is to provide a process which allows the compound of formula 1 to be synthesised on

DETAILED DESCRIPTION OF THE INVENTION

The present invention relates to a method for the large-scale preparation of the compound of formula

*[Structure of compound 1: ethyl 3-((2-(((4-carbamimidoylphenyl)amino)methyl)-1-methyl-1H-benzo[d]imidazole-5-carboxamido)(pyridin-2-yl)amino)propanoate with p-toluenesulfonic acid]*

1

*[p-toluenesulfonic acid structure with SO₃H and CH₃]*

X characterised in that a diamine of formula 2

*[Structure of compound 2]*

2 is reacted, by reaction with an oxadiazolone of formula 3

*[Structure of compound 3]*

3 to obtain a compound of formula 4

*[Structure of compound 4]*

4 which, without being isolated, is converted into the amidine of formula 1 by hydrogenation and the addition of p-toluenesulphonic acid and ammonia.

The starting compounds of formulae 2 and 3 may be prepared by the method described in WO 2006/000353.

For the reaction according to the invention, 2 and 3 are dissolved in an inert organic solvent and condensed in the presence of a water-binding agent.

The inert organic solvent used is preferably an aprotic solvent. Aprotic solvents are selected for example from among aliphatic or aromatic, optionally halogenated hydrocarbons, ethers, amides or mixtures thereof. Aprotic apolar solvents used are preferably branched or unbranched $C_5$-$C_8$ aliphatic alkanes, $C_4$-$C_{10}$ cycloalkanes, $C_1$-$C_6$ aliphatic haloalkanes, $C_6$-$C_{10}$ aromatic alkanes or mixtures thereof. Particularly preferred are alkanes such as pentane, hexane or heptane, cycloalkanes such as cyclohexane or methylcyclohexane, haloalkanes such as dichloromethane, aromatic alkanes such as benzene, toluene or xylene or mixtures thereof. Other suitable aprotic solvents are polar ethers such as for example tetrahydrofuran (THF), methyltetrahydrofuran, dioxane, tert-butyl-methylether or dimethoxyethylether or amides such as for example dimethylformamide, or lactams such as N-methylpyrrolidone, for example.

Water-binding agents that may be used include hygroscopic salts, inorganic or organic acids or the acid chlorides thereof, anhydrides of inorganic or organic acids, anhydrides of alkanephosphonic acids, molecular sieves or urea derivatives. 1,1'-carbonyldiimidazoles and alkanephosphonic anhydrides are preferred, while alkanephosphonic anhydrides are particularly preferred. Of the latter, according to the invention particular importance attaches to propanephosphonic anhydride (PPA=2,4,6-tripropyl-[1,3,5,2,4,6]trioxatriphosphinane 2,4,6-trioxide).

If alkanephosphonic anhydrides are used, preferably an organic base, particularly preferably a tertiary amine, particularly preferably diisopropylethylamine is added according to the invention.

Preferably 0.5-2.5 l (liters), particularly preferably 1.0-2.0 l, more preferably 1.3-1.5 l of the above-mentioned inert organic solvent are used per mol of the compound of formula 2 used.

Preferably, at least stoichiometric amounts of the compound of formula 3 are used per mol of the compound of formula 2 used. Particularly preferably, the compound of formula 3 is used in a slight excess. 1.0-2.0 mol, particularly preferably 1.0-1.5 mol, particularly preferably 1.1-1.3 mol of the compound of formula 3 are used per mol of the compound of formula 2 used.

The compounds 2 and 3 are dissolved in the above-mentioned inert, organic solvent at 10-50° C., preferably at 20-40°

C., particularly preferably at 25-35° C. Then, in the particularly preferred embodiment of the invention, the tertiary amine is added at constant temperature. Preferably, at least stoichiometric amounts of the tertiary amine are used per mol of the compound of formula 2 used. Particularly preferably, however, the tertiary amine is used in a large excess. Accordingly, 1.5-5.0 mol, particularly preferably 2.0-4.0 mol, particularly preferably 2.3-2.7 mol of the tertiary amine are used per mol of the compound of formula 2 used.

After the addition of the tertiary amine has ended, the alkanephosphonic anhydride, preferably PPA, is preferably metered in at a temperature in the range from 10-40° C., particularly preferably at 20-30° C. Preferably at least stoichiometric amounts of the alkanephosphonic anhydride are used per mol of the compound of formula 2 used. Particularly preferably, the alkanephosphonic anhydride is used in a slight excess. Particularly preferably, 1.0-2.0 mol, particularly preferably 1.0-1.7 mol, particularly preferably 1.1-1.4 mol of the alkanephosphonic anhydride are used per mol of the compound of formula 2 used. The PPA that is preferably used according to the invention is preferably added in dilute form. In a preferred embodiment, for the addition, it is taken up in the inert organic solvent used. Particularly preferably, the PPA is added in a solution containing 30-60% by weight (wt.-%), preferably 50% of tetrahydrofuran or ethyl acetate.

Once the addition of PPA has ended, the mixture is stirred for about another 0.25-4 h at constant temperature. Then preferably at least 0.5 equivalents of a weak organic acid are added, based on the compound 2 used. The weak organic acid is preferably citric or acetic acid. The acid may also be used in excess. Accordingly, 0.5-4.0 equivalents, particularly preferably 1.0-3 equivalents, particularly preferably 1.0-2.0 equivalents of the acid are used per mol of the compound of formula 2 used. Optionally the reaction mixture may be diluted with one of the above-mentioned inert organic solvents, preferably with the same solvent. For the dilution, preferably up to 50%, particularly preferably 10-30% of the quantity of solvent already put in are added.

After the addition of the acid and optionally dilution, the condensation to obtain the compound 4 is carried out at elevated temperature and optionally elevated pressure. According to the invention the temperature is preferably kept in the range above 50° C., preferably at 60-100° C., particularly preferably at 65-85° C. If a solvent that boils in this temperature range is used, the pressure is increased so that the reaction may be carried out at the specified temperature, in spite of the lower boiling point. Preferably, the pressure at which the reaction is carried out is adjusted to a value of 1-3 bar.

The course of the reaction is monitored by conventional methods, for example by thin layer chromatography or HPLC. After the reaction the reaction mixture is slowly cooled, preferably to a temperature in the range from 10-50° C., particularly preferably to about 20-30° C.

Without any further working up a suitable hydrogenation catalyst is now added to the reaction mixture. Suitable hydrogenation catalysts are generally transition metals such as for example nickel, platinum or palladium or the salts or oxides thereof. Preferred catalysts are Raney nickel, platinum oxide and palladium on an inert carrier material, particularly palladium on activated charcoal (Pd/C).

In a preferred embodiment, water-moistened 10% Pd/C is used. Preferably about 2-35 g, particularly preferably about 4-25 g, particularly preferably about 8-18 g of this catalyst are used per mol of the compound of formula 2 used.

After the addition of the hydrogenation catalyst, water is added. The amount of water added is preferably determined according to the total quantity of inert organic solvent used. Preferably, the amount of water added is 50-100% (v/v), particularly preferably 70-90% (v/v) of the total amount of solvent used.

After the addition of water, the reaction mixture is heated to a temperature in the range from 30-70° C., particularly preferably about 40-60° C. and is hydrogenated with stirring under a hydrogen pressure of about 2-6 bar, preferably 3-5 bar.

After the reaction the catalyst is filtered off, the filtrate is optionally diluted with about 5-30% of the quantity of water used previously, and para-toluenesulphonic acid is added at a temperature in the range from 10-60° C., particularly preferably about 20-40° C. The para-toluenesulphonic acid may be added as a solid, optionally in the form of the monohydrate thereof or in aqueous solution. Preferably, at least stoichiometric amounts of the para-toluenesulphonic acid are used per mol of the compound of formula 2 used. Particularly preferably, the para-toluenesulphonic acid is used in a slight excess. Particularly preferably 1.0-2.0 mol, particularly preferably 1.0-1.7 mol, particularly preferably 1.0-1.4 mol, particularly preferably 1.1-1.3 mol of para-toluenesulphonic acid are used per mol of the compound of formula 2 used.

Then ammonia is added, either in gaseous form or in the form of aqueous solutions. Preferably, according to the invention, the ammonia is used in the form of aqueous solutions, particularly preferably in the form of an aqueous solution containing about 25% (w/w) ammonia ($NH_4OH$). The addition may be carried out for example at a temperature in the range from 30-65° C. At this point preferably 2-20 mol, particularly preferably 6-16 mol, particularly preferably about 9-13 mol of ammonia are added per mol of the compound of formula 2 used.

During the addition of the ammonia, compound 1 begins to crystallise out. The reaction mixture is cooled to a temperature in the range from 0-40° C., particularly preferably to about 15-25° C. cooled, the compound 1 is filtered off and washed with water or acetone. More ammonia may optionally be added to the mother liquor in order to crystallise out further compound 1. If more ammonia is added at this point, this preferably amounts to 1-10 mol, particularly preferably 2-8 mol, particularly preferably about 3-5 mol ammonia per mol of the compound of formula 2 used.

Surprisingly, the addition of the ammonia causes the compound 1 to be almost totally precipitated from the reaction mixture. This results in a number of advantages over the processes known in the art, some of which are mentioned below. The yield of compound 1 is increased significantly. There is no need for any hot filtration to eliminate impurities 5 in the preparation of the intermediate 4. Moreover, less solvent and reagents are needed, which makes the synthesis much easier to carry out, particularly on an industrial scale. Furthermore, by contrast with the prior art, the time-consuming isolation and drying of an intermediate can be dispensed with.

The following abbreviations are used in the foregoing and hereinafter:
AcOH acetic acid
DIPEA N,N-diisopropylethylamine
EtOAc ethyl acetate
Pd/C palladium on activated charcoal
PPA propanephosphonic anhydride
PTSA p-toluenesulphonic acid
RT room temperature
THF tetrahydrofuran The following Examples serve to illustrate a synthesis process carried out by way of example. They are intended solely as examples of possible procedures without restricting the invention to their contents.

EXAMPLE 1

24.20 g of 2 and 19.95 g of 3 are largely dissolved in 100 ml THF at approx. 30° C. 24.92 g of DIPEA are then added at this temperature. Then 57.89 g of a 50% solution of PPA in THF are metered in at RT and the mixture is stirred for approx. 2 h. After the addition of 13.44 g of citric acid and 20 ml THF, condensation is carried out at approx. 90° C. under pressure to obtain the non-isolated intermediate 4. After the reaction has taken place the reaction mixture is cooled to RT and combined with 1.21 g of water-moistened 10% Pd/C and 100 ml of water. Then the suspension is heated to approx. 50° C. and hydrogenated under a hydrogen atmosphere (at approx. 4 bar).

Pd/C is filtered off and washed with 25 ml of water. After the addition of 25 ml of water the reaction mixture is combined at approx. 50° C. with 20.40 g of a 65% aqueous PTSA solution and 60 ml of a 25% aqueous ammonia solution. The tosylate begins to precipitate out. It is cooled to RT, the product 1 is filtered off and washed with water. Drying is carried out at 60° C. or up to 95° C. in vacuo.

Yield: 41.4 g of (87.2%)
Purity: >99% HPLC peak area

EXAMPLE 2

24.20 g of 2 and 19.95 g of 3 are largely dissolved in 87 ml THF at RT. At this temperature 24.92 g of DIPEA are then added. Then at RT 57.89 g of a 50% solution of PPA in THF are metered in, rinsed with 13 ml THF and stirred for approx. 2 h. After the addition of 6.72 g of citric acid and 20 ml THF condensation to obtain the non-isolated intermediate 4 is carried out at approx. 90° C. under pressure. After the reaction has taken place the reaction mixture is cooled to RT and combined with 1.24 g of water-moistened 10% Pd/C and 60 ml of water. Then the suspension is heated to approx. 50° C. and hydrogenated under a hydrogen atmosphere (at approx. 4 bar).

Pd/C is filtered off and washed with 50 ml of a THF-water mixture (7:3). After the addition of 20 ml of a THF-water mixture (7:3) the reaction mixture is combined at approx. 50° C. with 39.93 g of solid PTSA and 60 ml of a 25% aqueous ammonia solution. The tosylate begins to precipitate out. It is cooled to RT, the product 1 is filtered off and washed with water.

Drying is carried out at 40° C. or up to 95° C. in vacuo.
Yield: 42.2 g of (88.9%); purity: >99% HPLC peak area

EXAMPLE 3

24.20 g of 2 and 19.95 g of 3 are largely dissolved in 87 ml THF at RT. At this temperature 24.92 g of DIPEA are then added. Then at RT 57.89 g of a 50% solution of PPA in EtOAc are metered in, rinsed with 13 ml THF and stirred for approx. 2 h. After the addition of 6.72 g of citric acid and 20 ml THF condensation to obtain the non-isolated intermediate BIBR 1048 oxa-amidine is carried out at approx. 90° C. under pressure. After the reaction has taken place the reaction mixture is cooled to RT and combined with 1.21 g of water-moistened 10% Pd/C and 75 ml of water. Then the suspension is heated to approx. 50° C. and hydrogenated under a hydrogen atmosphere (at approx. 4 bar).

Pd/C is filtered off and washed with 50 ml of a THF-water mixture (1:1). After the addition of 25 ml THF and 10 ml of water the reaction mixture is combined at approx. 50° C. with 39.93 g of solid PTSA and 60 ml of a 25% aqueous ammonia solution. The tosylate begins to precipitate out. It is cooled to RT, the product 1 is filtered off and washed with water.

Drying is carried out at 40° C. or up to 95° C. in vacuo.
Yield: 43.1 g of (90.8%); purity: >99% HPLC peak area

EXAMPLE 4

24.20 g of 2 and 19.95 g of 3 are largely dissolved in 87 ml THF at RT. At this temperature 24.92 g of DIPEA are then added. Then at RT 57.89 g of a 50% solution of PPA in EtOAc are metered in, rinsed with 13 ml THF and stirred for approx. 2 h. After the addition of 4.20 g of AcOH and 20 ml THF condensation to obtain the non-isolated intermediate 4 is carried out at approx. 90° C. under pressure. After the reaction has taken place the reaction mixture is cooled to RT and combined with 1.25 g of water-moistened 10% Pd/C and 60 ml of water. Then the suspension is heated to approx. 50° C. and hydrogenated under a hydrogen atmosphere (at approx. 4 bar). Pd/C is filtered off and washed with 50 ml of a THF-water mixture (1:1). After the addition of 20 ml of a THF-water mixture the reaction mixture is combined at approx. 50° C. with 39.93 g of solid PTSA and 60 ml of a 25% aqueous ammonia solution. The tosylate begins to precipitate out. It is cooled to RT, the product 1 is filtered off and washed with water. Drying is carried out at 45° C. or up to 95° C. in vacuo.

Yield: 36.4 g of (76.7%); purity: >99% HPLC peak area

EXAMPLE 5

24.20 g of 2 and 19.95 g of 3 are largely dissolved in 86 ml THF at approx. 30° C. At this temperature 24.92 g of DIPEA are then added. Then at RT 57.89 g of a 50% solution of PPA in THF are metered in and stirred for approx. 2 h. After the addition of 10.50 g of L-tartaric acid and 20 ml THF condensation to obtain the non-isolated intermediate 4 is carried out at approx. 90° C. under pressure. After the reaction has taken place the reaction mixture is cooled to RT and combined with 1.21 g of water-moistened 10% Pd/C and 100 ml of water. Then the suspension is heated to approx. 50° C. and hydrogenated under a hydrogen atmosphere (at approx. 4 bar). Pd/C is filtered off and washed with 30 ml of water. After the addition of 20 ml of water the reaction mixture is combined at approx. 50° C. with 22.25 g of a 65% aqueous PTSA solution and 60 ml of a 25% aqueous ammonia solution. The tosylate begins to precipitate out. It is cooled to RT, the product 1 is filtered off and washed with water. Drying is carried out at 90° C. or up to 95° C. in vacuo.

Yield: 39.3 g of (82.8%); purity: >99% HPLC peak area.

EXAMPLE 6

24.20 g of 2 and 19.95 g of 3 are largely dissolved in 100 ml THF at approx. 30° C. At this temperature 23.07 g of DIPEA are then added. Then at 25° C. 57.89 g of a 50% solution of PPA in THF are metered in and stirred for approx. 30 min. After the addition of 20.17 g of citric acid and 20 ml THF condensation to obtain the non-isolated intermediate 4 is carried out at approx. 75° C. under pressure. After the reaction has taken place the reaction mixture is cooled to RT and combined with 1.21 g of water-moistened 10% Pd/C and 100 ml of water. Then the suspension is heated to approx. 50° C. and hydrogenated under a hydrogen atmosphere (at approx. 4 bar). Pd/C is filtered off and washed with 30 ml of water. After the addition of 20 ml of water the reaction mixture is combined at 28-38° C. with 22.25 g of a 65% aqueous PTSA solution. Then at 38° C. up to reflux temperature (64-65° C.) 60 ml of a 25% aqueous ammonia solution is metered in. The tosylate begins to precipitate out. It is cooled to RT and a further 20 ml of a 25% aqueous ammonia solution are added. The product 1 is filtered off and washed with water. Drying is carried out at 60° C. or up to 95° C. in vacuo.

Yield: 42.4 g of (89.3%); purity: >99% HPLC peak area

The invention claimed is:

1. A process for preparing a compound of formula 1

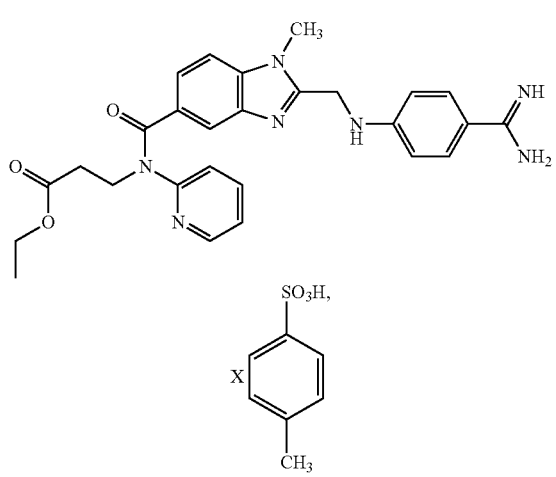

comprising the steps of:
reacting a diamine of formula 2

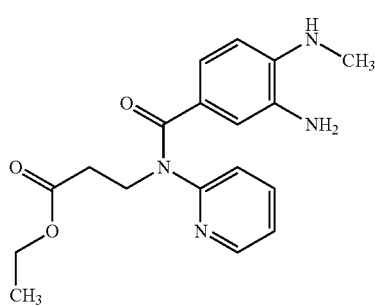

with an oxadiazolone of formula 3

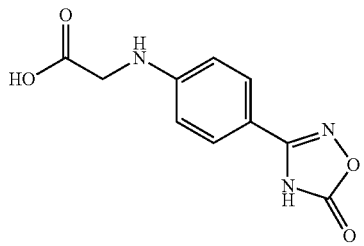

to form a compound of formula 4 and without being isolated,
converting the compound of formula 4 into the amidine of formula 1 by hydrogenation and addition of p-toluenesulphonic acid and ammonia.

2. The process according to claim 1, wherein the reaction of 2 and 3 to obtain the intermediate compound 4 is carried out in an inert organic solvent in the presence of a water-binding agent.

3. The process according to claim 2, wherein the solvent is an aprotic solvent that is selected from aliphatic or aromatic, optionally halogenated hydrocarbons, ethers, amides or mixtures thereof.

4. The process according to claim 2 or 3, wherein the water-binding agent is selected from hygroscopic salts, inorganic acids, organic acids, organic acid chlorides, anhydrides of inorganic acids, anhydrides of organic acids, anhydrides of alkanephosphonic acids, molecular sieves, urea derivatives and alkanephosphonic anhydrides.

5. The process according to claim 4, wherein the water-binding agent is selected from 1,1'-carbonyldiimidazole and propanephosphonic anhydride.

* * * * *